US00PP13326P2

(12) United States Plant Patent
Fruehwirth

(10) Patent No.: US PP13,326 P2
(45) Date of Patent: Dec. 10, 2002

(54) POINSETTIA PLANT NAMED 'ECKAYKIN'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,329

(22) Filed: Sep. 30, 2001

(51) Int. Cl.[7] ..... A01H 5/00
(52) U.S. Cl. ..... Plt./303
(58) Field of Search ..... Plt./303

(56) References Cited

U.S. PATENT DOCUMENTS

PP8,771 P * 6/1994 Fruehwirth ..... Plt./303

PP11,126 P * 11/1999 Fruehwirth ..... Plt./307

OTHER PUBLICATIONS

UPOV ROM GTITM Computer Database, GIT Jouve Retrieval Software 2002/02 Citation(s) for 'Eckaykin'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Poinsettia plant named 'Eckaykin', characterized by its inflorescences with dark red-colored flower bracts with random pink flecking; dark green-colored leaves with red-colored petioles; uniform and mounded plant habit; early flowering; and good post-production longevity.

2 Drawing Sheets

BOTANICAL CLASSIFICATION

*Euphoriba pulcherrima.*

BACKGROUND OF THE INVENTION

The present Invention relates to a new and distinct cultivar of Poinsettia plant, botanically known as *Euphorbia pulcherrima* Willd., and hereinafter referrred to by the name 'Eckaykin'.

The new Poinsettia is a naturally-occurring whole plant mutation of a unnamed proprietary induced mutation, not patented, that originated by exposing unrooted cuttings of the *Euphorbia pulcherrima* Willd. cultivar 721, disclosed in U.S. Plant Pat. No. 11,126, to gamma radiation. The new Poinsettia was discovered and selected by the Inventor as a single plant within a population of plants of the irradiated selection in 1999 in a controlled environment in Encinitas, Calif.

Asexual reproduction of the new Poinsettia by terminal cuttings taken at Encinitas, Calif., since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaykin', These characteristics in combination distinguish 'Eckaykin' as a new and distinct cultivar:

1. Inflorescences with dark red-colored flower bracts with random pink flecking.

2. Dark green-colored leaves with red-colored petioles.

3. Uniform and mounded plant habit.

4. Early flowering, natural season flower maturity date is November 26 for plants grown in Encinitas, Calif.; response time, about 8.5 weeks.

5. Good post-production longevity.

Plants of the new Poinsettia can be compared to plants of the cultivar 721. In side-by-side comparisons conducted in Encinitas, Calif., plants of the new Poinsettia differed primarily from plants of the cultivar 721 in flower bract coloration as flower bracts of plants of the cultivar 721 were solid red-colored.

Plants of the new Poinsettia can also be compared to plants of the cultivar 490 Jingle Bells, disclosed in U.S. Plant Pat. No. 8,771. In side-by-side comparisons conducted in Encinitas, Calif., plants of the new Poinsettia differed primarily from plants of the cultivar 490 Jingle Bells in the following characteristics:

1. Plants of the new Poinsettia were more outwardly spreading than plants of the cultivar 490 Jingle Bells.

2. Plants of the new Poinsettia had slightly larger leaves and shorter petioles than plants of the cultivar 490 Jingle Bells.

3. Flower bracts of plants of the new Poinsettia were mostly horizontal whereas flower bracts of the cultivar 490 Jingle Bells were drooping.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Eckaykin' grown in a 16.5-cm container.

The photograph at the top of the second sheet comprises a top perspective view of a typical flowering plant of 'Eckaykin'.

The photograph at the bottom of the second sheet is a close-up view of typical leaves and flower bracts of 'Eckaykin' (left) and '490 Jingle Bells' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 17.5 weeks from unrooted cuttings when the photographs and the detailed botanical description were taken.

In the following description, color references are made to The Royal Horticultural Society Colour Chart except where general terms of ordinary dictionary significance are used.

Botanical classification: *Euphorbia pulcherrima* Willd. cultivar Eckaykin.

Parentage: Naturally-occuring whole plant mutation of a unnamed proprietary *Euphorbia pulcherrima* Willd. induced mutation, not patented.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous and freely-branching.

Plant description:

*Plant form.*—Inverted triangle, top of plant rounded and mounding.

*Growth habit.*—Upright and uniform plant habit. Moderate vigor.

*Plant height.*—About 22 cm.

*Plant diameter or spread.*—About 35 cm.

*Lateral branch description.*—Quantity: About five lateral branches develop after pinching. Length: About 19 cm. Diameter: About 6 mm. Internode length: About 1.75 cm. Color: 146A.

*Foliage description.*—Arrangement: Alternate, single. Quantity of leaves per lateral branch: About eight. Length: About 12 cm. Width: About 8.5 cm. Shape: Elliptic with irregular shallow lobing. Apex: Acuminate. Base: Acute. Margin: Entire with irregular shallow lobing. Venation pattern: Pinnate. Texture: Upper surface: Glabrous. Lower surface: Slightly pubescent. Surface: Mostly flat. Color: Young foliage, upper surface: 147A. Young foliage, lower surface: 147B. Fully expanded foliage, upper surface: Darker than 147A. Fully expanded foliage, lower surface: 147A. Venation, upper surface: 147B. Venation, lower surface: 147C. Petiole: Length: About 4.5 cm. Diameter: About 2 mm. Color: 59B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Nothern Hemisphere. Flower initiation and development is induced under long nyctoperiod conditions. Response time, about 8.5 weeks; natural season flower maturity date is November 26 for plants grown in Encinitas, Calif.

*Post-production longevity.*—Plants of the new Poinsettia maintain good substance and bract color for about three to four weeks under interior conditions.

*Quantity of inflorescences per plant.*—One per lateral branch, about five.

*Inflorescence size.*—Diameter: About 28 cm. Height (depth): About 5 cm.

*Flower bracts.*—Quantity of flower bracts per inflorescence: About 28. Length, largest bracts: About 12 cm. Width, largest bracts: About 7.5 cm. Shape: Elliptic with irregular shallow lobing. Apex: Acuminate. Base: Acute. Margin: Entire with irregular shallow lobing. Texture, upper and lower surfaces: Glabrous, velvety. Surface: Mostly flat. Orientation: Horizontal to slightly drooping. Color: Developing or transitional bracts, upper surface: Irregular and random areas of 46A and darker than 147A with random flecks of 50A, then becoming mostly 46A with random flecks of 50A. Developing or transitional bracts, lower surface: Irregular and random areas of 46B and 147A, then becoming mostly 46B. Fully developed bracts, upper surface: 46A with random flecks of 51B; color does not fade with subsequent development. Fully developed bracts, lower surface: 46C with random flecks of 51C. Venation, upper and lower surfaces: Same as ground color. Bract petiole: Length: About 4.2 cm. Diameter: About 2 mm. Color: 60B.

*Cyathia.*—Quantity: About 20 per corymb. Diameter of cyathia cluster: About 4 by 4.5 cm. Length: About 1 cm. Width: About 6 mm. Shape: Ovoid. Color: Immature: 144A. Mature: 144B to 144C. Peduncle: Length: About 3 mm. Diameter: About 2 mm. Aspect: Strong, erect. Color: 144C. Stamens: Stamen number: About 10 per cyathium. Anther shape: Oval. Anther length: Less than 1 mm. Anther color: 46A. Amount of pollen: Scarce. Pollen color: 14A. Pistils: Pistil number: One per cyathium. Pistil length: About 8 mm. Stigma shape: Three-parted. Stigma color: 46A. Style length: About 3 mm. Style color: 144C. Ovary color: 144B. Nectary number: One per cyathia. Nectary color: 17A.

Disease/pest resistance: Resistance to pathogens and pests common to Poinsettias has not been observed on plants grown under commercial conditions.

It is claimed:

1. A new and distinct cultivar of Poinsettia plant named 'Eckaykin', as illustrated and described.

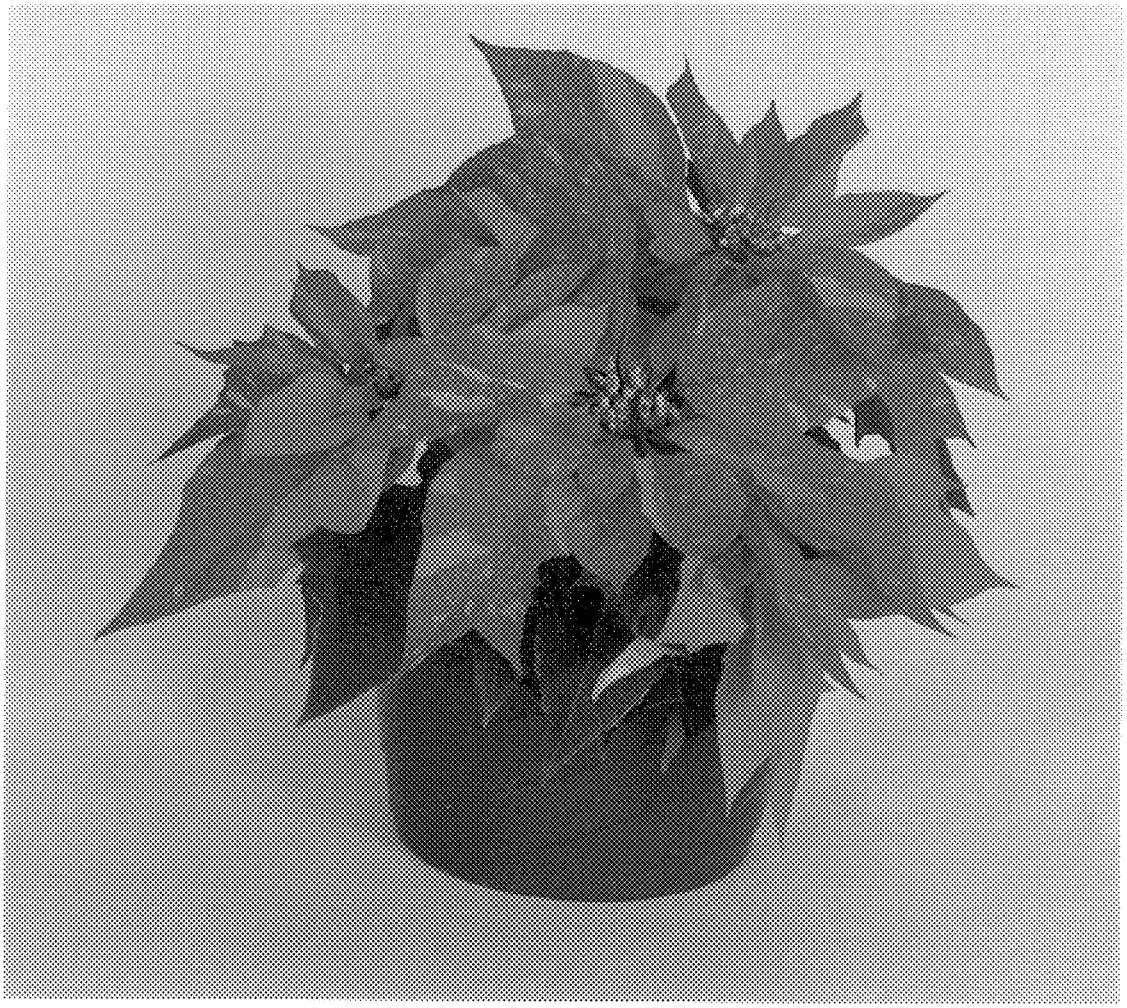

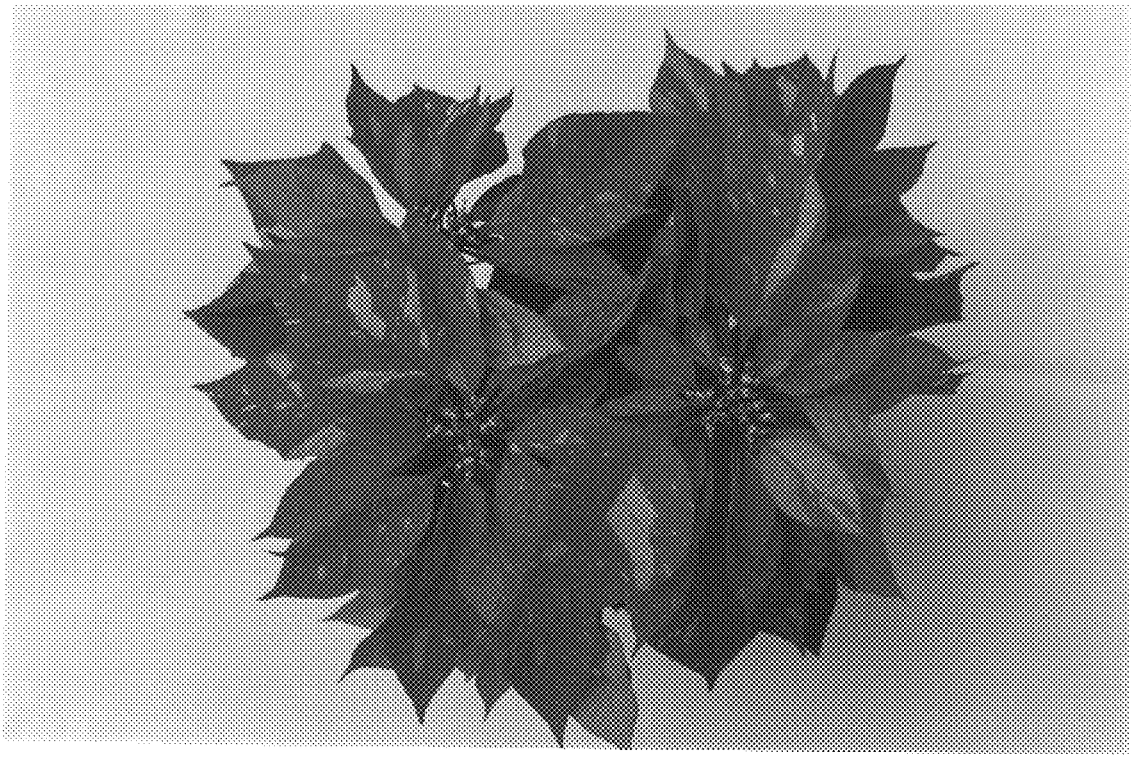
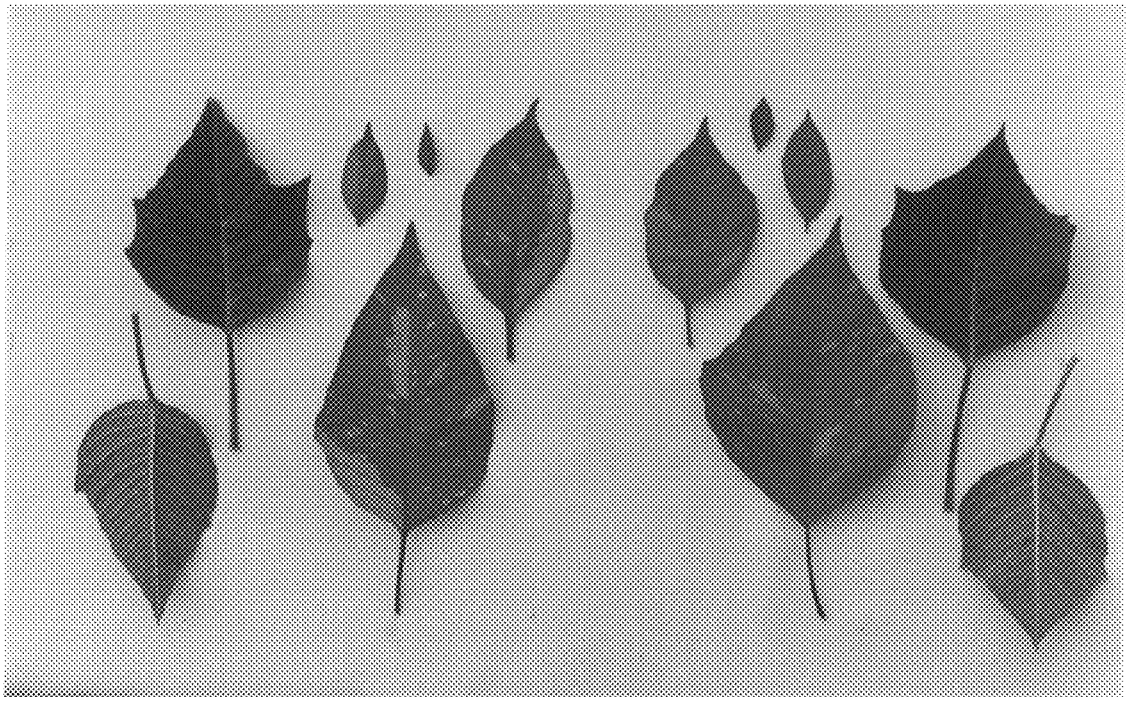

* * * * *